(12) United States Patent
Stevens et al.

(10) Patent No.: US 9,304,077 B2
(45) Date of Patent: Apr. 5, 2016

(54) INSPECTION APPARATUS AND METHOD

(75) Inventors: Lucas Henricus Johannes Stevens, Eindhoven (NL); Arno Jan Bleeker, Westerhoven (NL)

(73) Assignee: ASML Netherlands B.V., Veldhoven (NL)

( * ) Notice: Subject to any disclaimer, the term of this patent is extended or adjusted under 35 U.S.C. 154(b) by 1163 days.

(21) Appl. No.: 13/166,384

(22) Filed: Jun. 22, 2011

(65) Prior Publication Data

US 2012/0038910 A1   Feb. 16, 2012

Related U.S. Application Data

(60) Provisional application No. 61/359,110, filed on Jun. 28, 2010.

(51) Int. Cl.
| | | |
|---|---|---|
| *G01N 21/00* | (2006.01) | |
| *G01N 21/17* | (2006.01) | |
| *G01N 21/956* | (2006.01) | |

(52) U.S. Cl.
CPC ............ *G01N 21/1717* (2013.01); *G01N 21/00* (2013.01); *G01N 21/95623* (2013.01)

(58) Field of Classification Search
CPC .................... G01N 21/956; G01N 2021/4714; G01N 2021/8845
USPC ............................ 356/399–401, 237.1–237.5
See application file for complete search history.

(56) References Cited

U.S. PATENT DOCUMENTS

| | | | |
|---|---|---|---|
| 7,081,957 B2 | 7/2006 | Norton | |
| 7,633,689 B2 | 12/2009 | Shmarev et al. | |
| 8,325,323 B2 * | 12/2012 | Conradi | G03F 7/70891 |
| | | | 355/52 |
| 8,705,007 B2 * | 4/2014 | Cramer | G01J 3/18 |
| | | | 356/400 |
| 2009/0021714 A1 | 1/2009 | Mann et al. | |
| 2011/0069312 A1 | 3/2011 | Kandel et al. | |

FOREIGN PATENT DOCUMENTS

EP  1 628 164 B1  10/2010

* cited by examiner

*Primary Examiner* — Iyabo S. Alli
(74) *Attorney, Agent, or Firm* — Sterne, Kessler, Goldstein & Fox P.L.L.C.

(57) ABSTRACT

Ghost reflections in a catadioptric scatterometer objective are excluded from an angle-resolved spectrum measurement by using a partial pupil for illumination and for the measurement excluding the area of the pupil plane that has been illuminated. Ghost reflections are reflected back into same point in the pupil plane. The ghost reflections do not interfere with the signal in the non-illuminated area of the pupil plane. An illumination system provides a beam of electromagnetic radiation to illuminate a first area in an illumination pupil plane of the objective. The objective is arranged as to illuminate the substrate with the beam of electromagnetic radiation. The illumination pupil plane is the back projected image of the pupil plane of the objective and is also imaged into the measurement pupil plane at the back focal plane of the objective, via auxiliary optics. A detector is configured to measure an angle resolved spectrum arising from the illumination of the substrate, in a measurement area of the measurement pupil plane of the objective excluding an area corresponding to the first area.

16 Claims, 9 Drawing Sheets

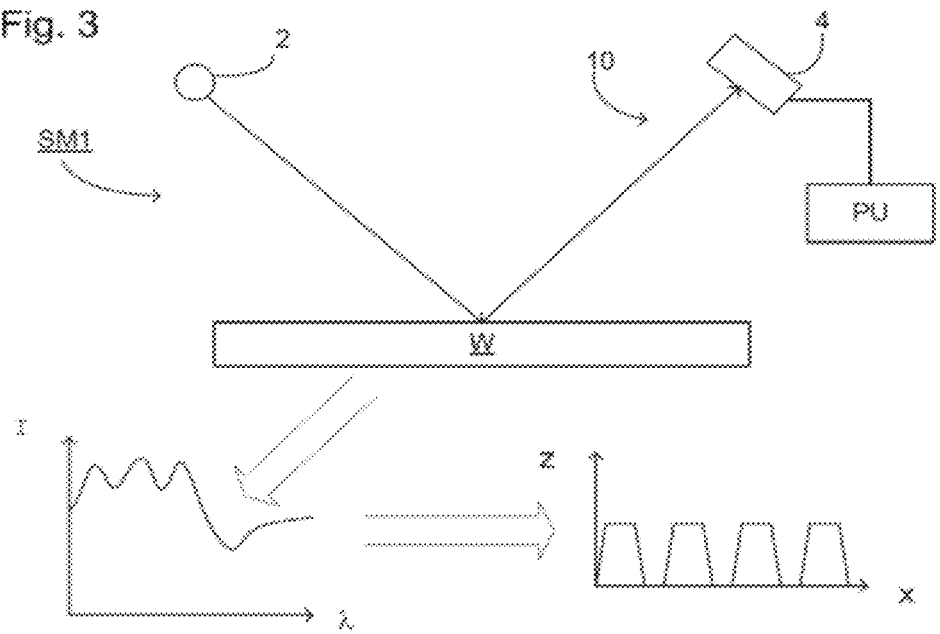
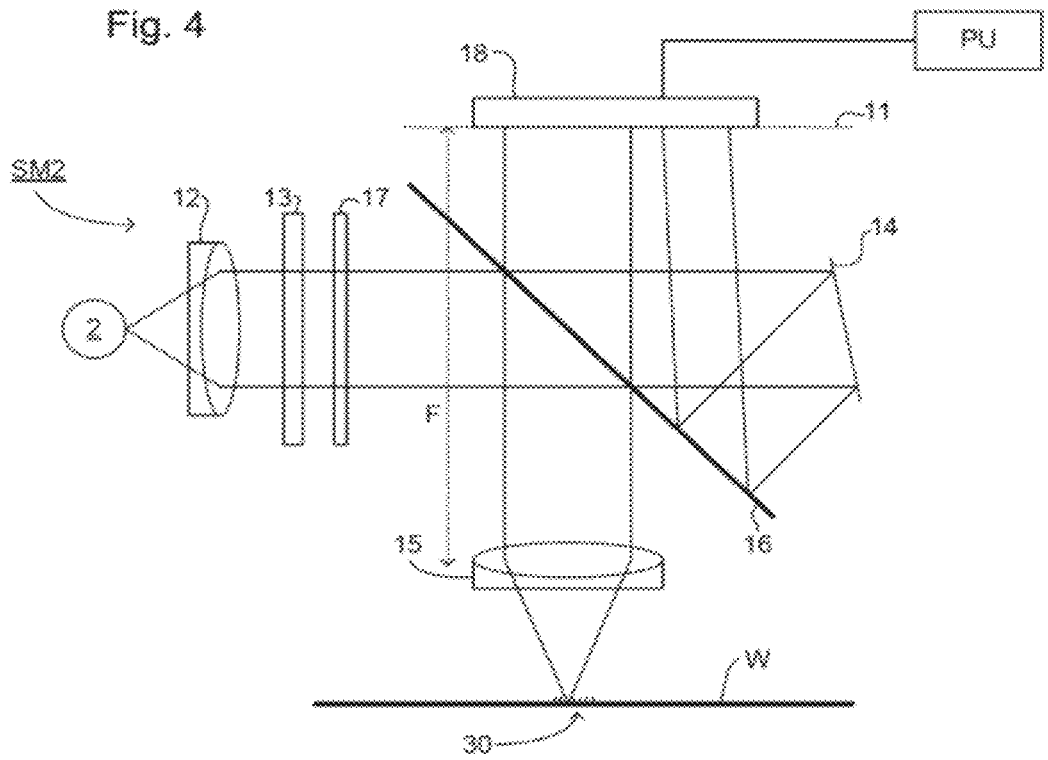

INSPECTION APPARATUS AND METHOD

CROSS REFERENCE TO RELATED APPLICATION

This application claims benefit under 35 U.S.C. 119(e) to U.S. Provisional Application No. 61/359,110, filed Jun. 28, 2010, which is incorporated by reference herein in its entirety.

BACKGROUND

1. Field of the Invention

The present invention relates to an inspection apparatus and methods of inspection usable, for example, in the manufacture of devices by lithographic techniques.

2. Related Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning" direction) while synchronously scanning the substrate parallel or anti parallel to this direction. It is also possible to transfer the pattern from the patterning device to the substrate by imprinting the pattern onto the substrate.

In order to monitor the lithographic process, parameters of the patterned substrate are measured. Parameters may include, for example, the overlay error between successive layers formed in or on the patterned substrate and critical linewidth of developed photosensitive resist. This measurement may be performed on a product substrate and/or on a dedicated metrology target. There are various techniques for making measurements of the microscopic structures formed in lithographic processes, including the use of scanning electron microscopes and various specialized tools. A fast and non-invasive form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

Catadioptric optical systems are useful for high numerical aperture objectives in scatterometers because they are compact and allow a wide range of illumination wavelengths. However, reflections at the glass to air interface in catadioptric optical systems used in scatterometers, called ghost reflections, result in unwanted detected signal in the angle-resolved spectrum. Anti-reflective coatings to suppress the ghost reflections are not available that are effective at the wide range of illumination wavelengths over which such scatterometers operate.

Two ghost reflections may be generated at the interfaces, the first order ghost reflection occurs before the illuminating radiation has reached the substrate. The first order ghost reflection is constant in time, has a uniform pupil plane fill, and magnitude of, for example, approximately 2-4% of the detected signal. The second order ghost reflection occurs after the illuminating radiation is reflected from the substrate. Radiation leaving the substrate is reflected back at the air-to-glass interface and via the substrate back into the optical system. The second order ghost reflections are subject to two interactions with the substrate. Therefore, depending on the substrate, the magnitude is much less than for first order ghost reflections, for example, approximately $4^{10-4}$ to $16^{10-4}$ of the detected signal.

SUMMARY

Therefore, what is needed is an effective system and method to address and overcome the effects of ghost reflections that result in unwanted detected signal in the angle-resolved spectrum.

In an embodiment of the present invention, there is provided an inspection apparatus for inspecting a substrate, the inspection apparatus including an illumination system configured to provide a beam of electromagnetic radiation by illuminating a first area in an illumination pupil plane of an objective, an objective arranged with the illumination system to illuminate the substrate with the beam of electromagnetic radiation, and a detector configured to measure an angle resolved spectrum arising from the illumination of the substrate, in a measurement area of a measurement pupil plane of the objective excluding an area corresponding to the first area.

In another embodiment of the present invention, there is provided method of inspecting a substrate, the method including the steps of providing a beam of electromagnetic radiation by illuminating a first area in an illumination pupil plane of an objective, illuminating the substrate with the beam of electromagnetic radiation via the objective, and measuring an angle resolved spectrum arising from the illumination of the substrate, in a measurement area of a measurement pupil plane of the objective excluding an area corresponding to the first area.

Further embodiments, features, and advantages of the present invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example only, with reference to the accompanying schematic drawings in which corresponding reference symbols indicate corresponding parts. Further, the accompanying drawings, which are incorporated herein and form part of the specification, illustrate the present invention, and, together with the description, further serve to explain the principles of the invention and to enable a person skilled in the relevant art(s) to make and use the invention.

FIG. 3 depicts a first scatterometer.

FIG. 4 depicts a second scatterometer.

Figure 1:
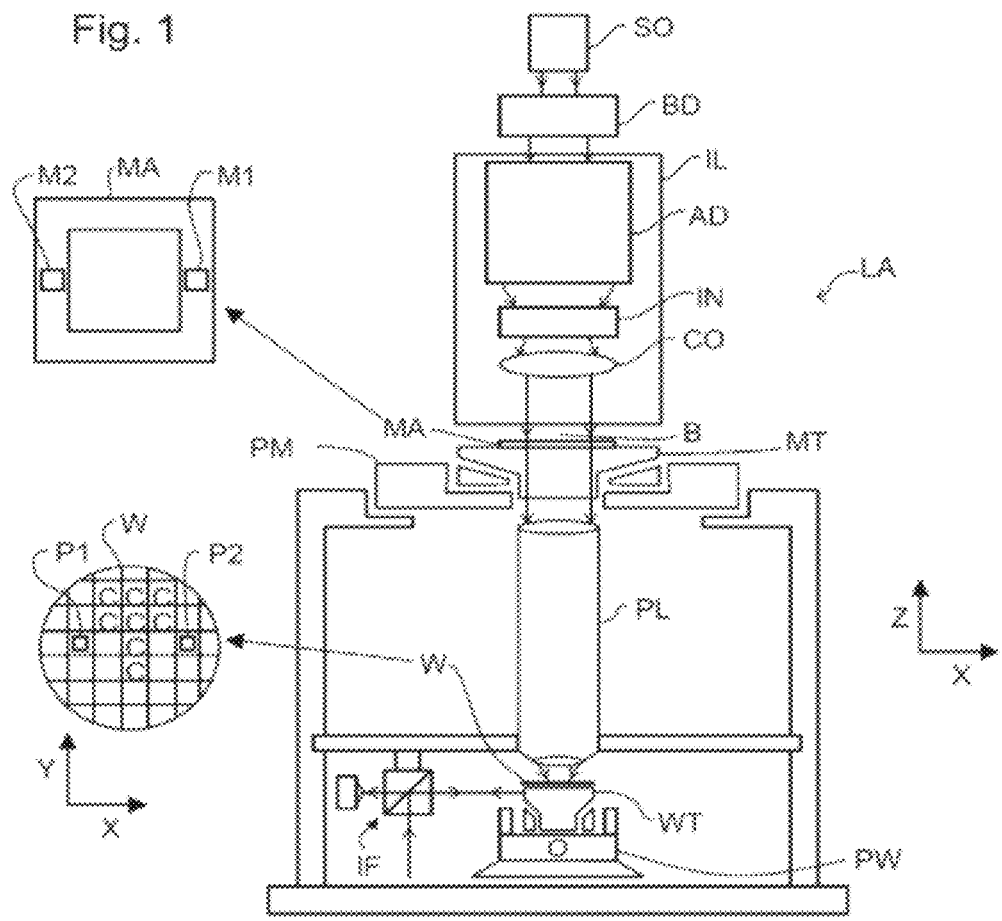
FIG. 1 depicts a lithographic apparatus.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment," "an embodiment," "an example embodiment," etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to affect such feature, structure, or characteristic in connection with other embodiments whether or not explicitly described.

Embodiments of the invention can be implemented in hardware, firmware, software, or any combination thereof. Embodiments of the invention can also be implemented as instructions stored on a machine-readable medium, which may be read and executed by one or more processors. A machine-readable medium can include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

FIG. 1, according to an embodiment of the present invention, schematically depicts a lithographic apparatus. The apparatus includes an illumination system (illuminator) IL configured to condition a radiation beam B (e.g., UV radiation or DUV radiation), a support structure (e.g., a mask table) MT constructed to support a patterning device (e.g., a mask) MA and connected to a first positioner PM configured to accurately position the patterning device in accordance with certain parameters, a substrate table (e.g., a wafer table) WT constructed to hold a substrate (e.g., a resist coated wafer) W and connected to a second positioner PW configured to accurately position the substrate in accordance with certain parameters, and a projection system (e.g., a refractive projection lens system) PL configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic, or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing various types of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system."

In this embodiment, for example, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables and for example, two or more mask tables. In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent, which are commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:
1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.
2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.
3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
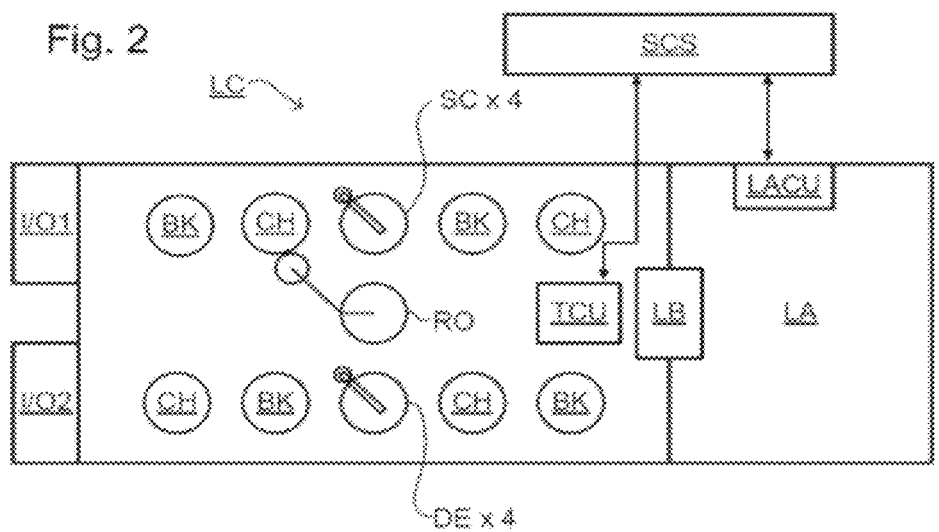
FIG. 2 depicts a lithographic cell or cluster.

As shown in FIG. 2 the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU that is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments, for example, can be made to exposures of subsequent substrates, especially if the inspection can be done soon and fast enough that other substrates of the same batch are still to be exposed. Also, already exposed substrates may be stripped and reworked to improve yield, or possibly be discarded, thereby avoiding performing exposures on substrates that are known to be faulty. In a case where only some target portions of a substrate are faulty, further exposures can be performed only on those target portions that are deemed to be non-faulty.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast, as in there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) that is customarily the first step carried out on exposed substrates and increases the contrast between exposed and unexposed parts of the resist. At this stage, the image in the resist may be referred to as semi-latent. It is also possible to make measurements of the developed resist image, at which point either the exposed or unexposed parts of the resist have been removed, or after a pattern transfer step such as etching. The latter possibility limits the possibilities for rework of faulty substrates but may still provide useful information.

FIG. 3 depicts a scatterometer. It comprises a broadband (white light) radiation projector 2 that projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g., by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Another scatterometer is shown in FIG. 4. In this device, the radiation emitted by radiation source 2 is collimated using lens system 12 and transmitted through interference filter 13 and polarizer 17, reflected by partially reflected surface 16 and is focused onto substrate W via a microscope objective lens 15, which has a high numerical aperture (NA), for example, preferably at least about 0.9 and more preferably at least about 0.95. Immersion scatterometers may even have lenses with numerical apertures over 1. The reflected radiation then transmits through partially reflecting surface 16 into a detector 18 in order to have the scatter spectrum detected. In one example, the detector may be located in the back-projected pupil plane 11, which is at the focal length of the lens system 15, however the pupil plane may instead be re-imaged with auxiliary optics (not shown in FIG. 4, but shown as 19 in FIG. 5) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18 or alternatively on to a different detector (not shown).

A set of interference filters 13 is available to select a wavelength of interest in the range of, for example, 405-790 nm or even lower, such as 200-300 nm. The interference filter can be tunable rather than comprising a set of different filters. A grating could be used instead of interference filters.

The detector 18 can measure the intensity of scattered light at a single wavelength (or narrow wavelength range), the intensity separately at multiple wavelengths or integrated over a wavelength range. Furthermore, the detector can separately measure the intensity of transverse magnetic- and transverse electric-polarized light and/or the phase difference between the transverse magnetic- and transverse electric-polarized light.

Using a broadband light source, i.e., one with a wide range of light frequencies or wavelengths, and therefore a wide range of colors is possible, which gives a large Etendue, allowing the mixing of multiple wavelengths. The plurality of wavelengths in the broadband preferably each has a bandwidth of $\Delta\lambda$ and a spacing of at least 2 $\Delta\lambda$ (i.e., twice the bandwidth). A plurality of "sources" of radiation can be different portions of an extended radiation source that have been split using fiber bundles. In this way, angle resolved scatter spectra can be measured at multiple wavelengths in parallel. A 3-D spectrum, for example, such as wavelength and two different angles can be measured, which contains more information than a 2-D spectrum. This allows more information to be measured that increases metrology process robustness. This is described in more detail in European Patent No. 1,628,164A, which is incorporated by reference herein in its entirety.

The target 30 on substrate W can be a 1-D grating, which is printed such that after development, the bars are formed of solid resist lines. The target 30 may be a 2-D grating, which is printed such that after development, the grating is formed of solid resist pillars or vias in the resist. The bars, pillars, or vias may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other scatterometry processes.

Figure 5:
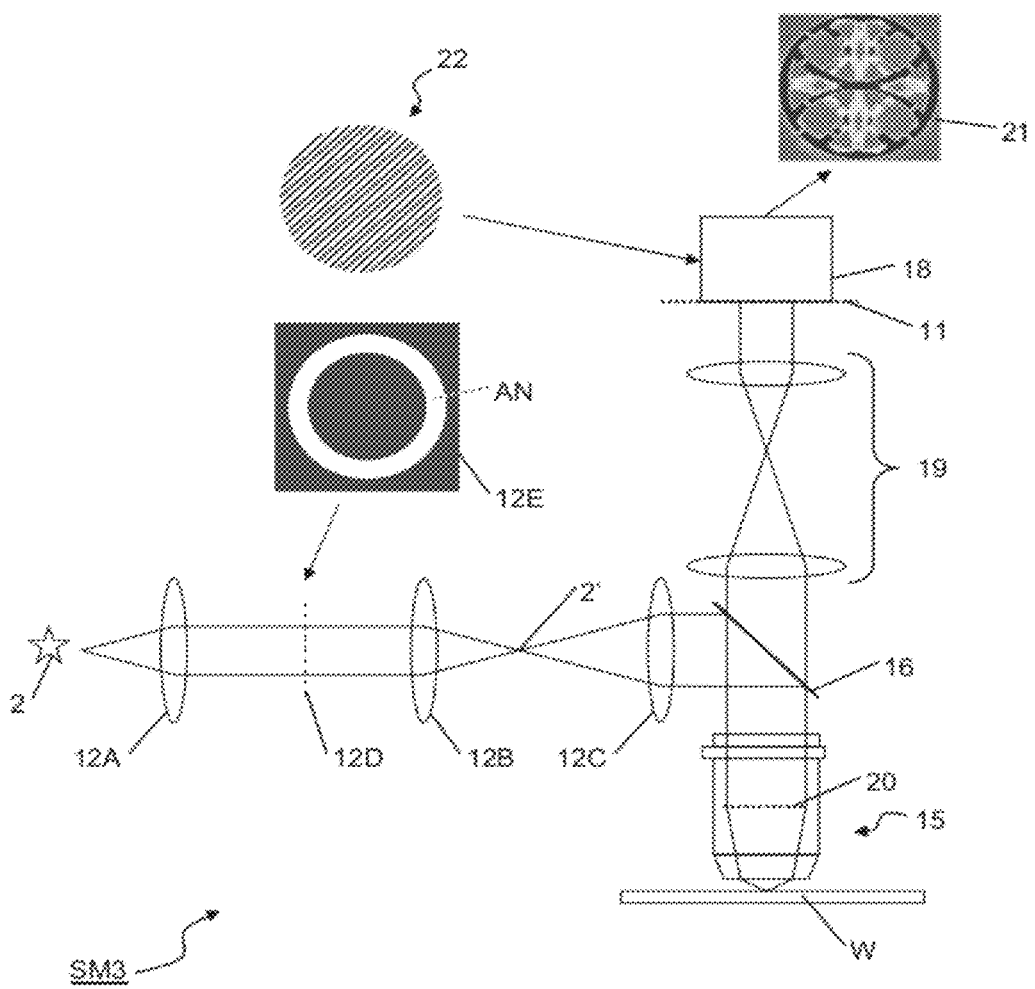
FIG. 5 depicts a third scatterometer with annular pupil illumination.

A further scatterometer inspection apparatus SM3, for inspecting a substrate W, is shown in FIG. 5. Elements in common with the scatterometer described with reference to FIG. 4 have the same labels. The illumination system of the scatterometer SM3 can be regarded as formed of two parts: a first part, including lenses 12A and 12B, forms an intermediate image 2' of the radiation source 2, while a second part, represented by lens 12C, works with the high-NA objective 15 to image the intermediate image 2' onto the substrate W. An illumination aperture blade 12E is provided in the first part of the illumination system in the illumination pupil plane 12D. The illumination pupil plane 12D is the back projected image of the pupil plane 20 of the objective. The objective pupil plane 20 is also imaged into the measurement pupil plane at the back focal plane 11 of the objective 15, via the auxiliary optics 19. The aperture blade 12D that defines an illumination mode, for example annular illumination, suitable for the intended measurement, e.g., overlay. Thus the illumination system is configured to provide a beam of electromagnetic radiation by illuminating an annular area AN in the illumination pupil plane 12D of the objective 15. The detector 18 is configured to measure an angle resolved spectrum 21 arising from the illumination of the substrate W, in a measurement area 22 of the measurement pupil plane 11. The measurement area 22 includes an area corresponding to the annular area AN.

There are several known designs of a catadioptric optical system as disclosed in U.S. Pat. No. 7,633,689, which is incorporated by reference herein in its entirety, and illustrated in FIGS. 6-8. In these Figures, the typical labeling of surfaces in the order they are encountered by incoming rays is used, that is s1, s2, s3, s4, etc. It should therefore be noted that, for example, s3 is not the same surface in each of FIGS. 6-8. In each of the arrangements depicted in FIGS. 6-8, collimated electromagnetic radiation from an illuminator is focused onto a small spot (such as approximately 10 microns) on a substrate (e.g., a wafer). Each arrangement can be used for scatterometry, and each arrangement has an extremely wide numerical aperture (such as a numerical aperture of approximately 0.95) and operates in a wide spectral range (such as about 200 nanometers to 1000 nanometers). Each of these arrangements is described in more detail below.

Figure 6:
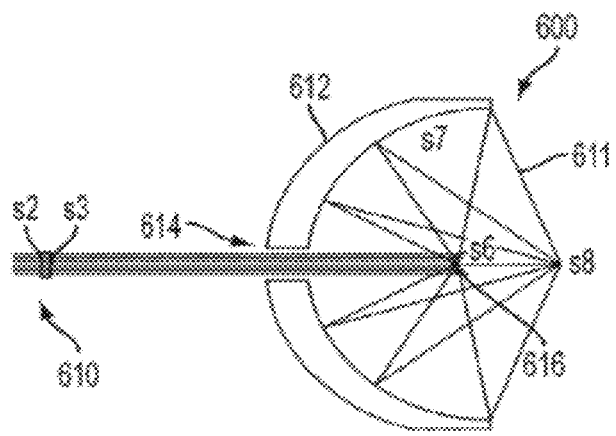
FIG. 6 depict a catadioptric optical objective.

FIG. 6 depicts an example catadioptric optical system 600. As shown in FIG. 6, catadioptric optical system 600 includes a correcting plate 610, a spherical convex mirror 616, and an aspherical concave mirror 612.

Correcting plate 610 conditions a beam of electromagnetic radiation to correct one or more optical aberrations (such as coma). As shown in FIG. 6, correcting plate 610 includes an aspherical surface s2 and a spherical surface s3.

Spherical convex mirror 616 comprises a spherical reflective surface s6 that is positioned to reflect the electromagnetic radiation conditioned by correcting plate 610. Electromagnetic radiation conditioned by correcting plate 610 passes through a hole 614 in aspherical concave mirror 612 and impinges on spherical convex mirror 616. Spherical convex mirror 616 can be positioned on mechanical supports in air with respect to a wafer (not specifically illustrated in FIG. 6).

Aspherical concave mirror 612 receives the electromagnetic radiation reflected by spherical reflective surface s6. Aspherical concave mirror 612 comprises an aspherical reflective surface s7 that focuses this electromagnetic radiation on a target portion of the wafer. For example, an example ray 611 reflected by aspherical reflective surface s7 is depicted in FIG. 6.

Figure 7:
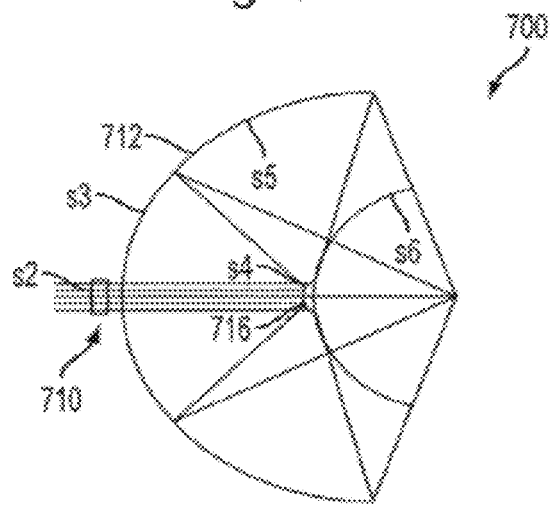
FIG. 7 depicts a catadioptric optical objective with a monolithic element.

FIG. 7 depicts an example catadioptric optical system 700. As shown in FIG. 7, catadioptric optical system 700 includes a correcting plate 710, a spherical convex mirror 716, and a monolithic glass element 712.

Correcting plate 710 conditions a beam of electromagnetic radiation to correct one or more optical aberrations (such as coma). Correcting plate 710 includes an aspherical surface s2.

Spherical convex mirror 716 comprises a spherical reflective surface s4 that is positioned to reflect the electromagnetic radiation conditioned by correcting plate 710. In the arrangement depicted in FIG. 7, spherical convex mirror 716 is positioned on a surface s6 of monolithic glass element 712. Aspheric surface s5 of monolithic glass element 712 has a transparent portion between correcting plate 710 and spherical convex mirror 716 to allow radiation to pass. The transparent portion is centered around the optical axis and has a diameter that is based the width of the input beam. The remainder of aspheric surface s5 is reflective. As a result, inside surface s5 (that is the same as outside surface s3) passes a beam coming from correcting plate 710, but reflects rays coming from spherical mirror 716. That is, electromagnetic radiation conditioned by correcting plate 710 passes through transparent portion of surface s5 in monolithic glass element 712 and impinges on spherical convex mirror 716.

Monolithic glass element 712 includes surfaces s4, s5 and s6. Surface s5 of monolithic glass element 712 receives the electromagnetic radiation reflected by spherical convex mirror 716 (surface s4) and reflects this electromagnetic radiation toward a target portion of the wafer. Before impinging on the target portion of the wafer, the electromagnetic radiation traverses surface s6 of monolithic glass element. Importantly, all rays reflecting off of aspheric reflective surface s5 exit monolithic glass element 712 perpendicular to surface s6, and are therefore not refracted by surface s6. As a result, catadioptric optical system 700 is achromatic.

The monolithic glass element 712 of the catadioptric optical system illustrated in FIG. 7 has the effect that the surface s4 can be positioned and fixed accurately during the manufacture of the monolithic glass element, instead of using the mechanical supports discussed with reference to FIG. 6.

Figure 8:
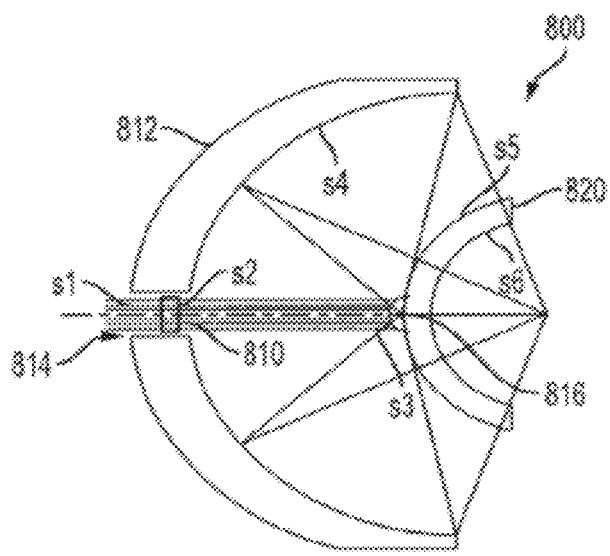
FIG. 8 depicts catadioptric optical objective with a spherical support element.

FIG. 8 depicts a further example catadioptric optical system 800. As shown in FIG. 8, catadioptric optical system 800 includes a correcting plate 810, a spherical convex mirror 816, an aspherical concave mirror 812, and a element 820.

Correcting plate 810 conditions a beam of electromagnetic radiation to correct one or more optical aberrations (such as coma). Correcting plate 810 includes an aspherical surface s1 and a surface s2. As illustrated in FIG. 8, correcting plate 810 is positioned in a hole 814 of aspherical concave mirror 812.

Spherical convex mirror 816 comprises a spherical reflective surface s3 that is positioned to reflect the electromagnetic radiation conditioned by correcting plate 810. In the arrangement depicted in FIG. 8, spherical convex mirror 816 is positioned on a surface s5 of element 820. Electromagnetic radiation conditioned by correcting plate 810 impinges on spherical convex mirror 816.

Aspherical concave mirror 812 includes aspheric reflective surface s4. Aspherical reflective surface s4 of aspherical concave mirror 812 receives the electromagnetic radiation reflected by spherical convex mirror 816 and reflects this electromagnetic radiation toward element 820 (e.g., a meniscus).

Element 820 includes a first surface s5 and a second surface s6. The electromagnetic radiation reflected by aspherical concave mirror 812 passes through element 820 perpendicular to both first surface s5 and second surface s6, and is therefore not refracted at either surface of element 820. As a result, catadioptric optical system 800 is achromatic.

The element 820 of the catadioptric optical system illustrated in FIG. 8 has the effect that the surface s4 can be held in place without the conventional mechanical supports that would block the radiation on its way to or from the wafer.

However, both the catadioptric optical systems illustrated in FIGS. 7 and 8 have a problem of ghost reflections when the electromagnetic radiation passes perpendicularly through surface s6 in FIG. 7 and surfaces s5 and s6 in FIG. 8.

Embodiments of the present invention use a partly filled pupil in illumination. Both first and second order ghost reflections are reflected back into same point in the pupil plane. The ghost reflections do not interfere with the signal in the non-illuminated area of the pupil plane.

Figure 9:
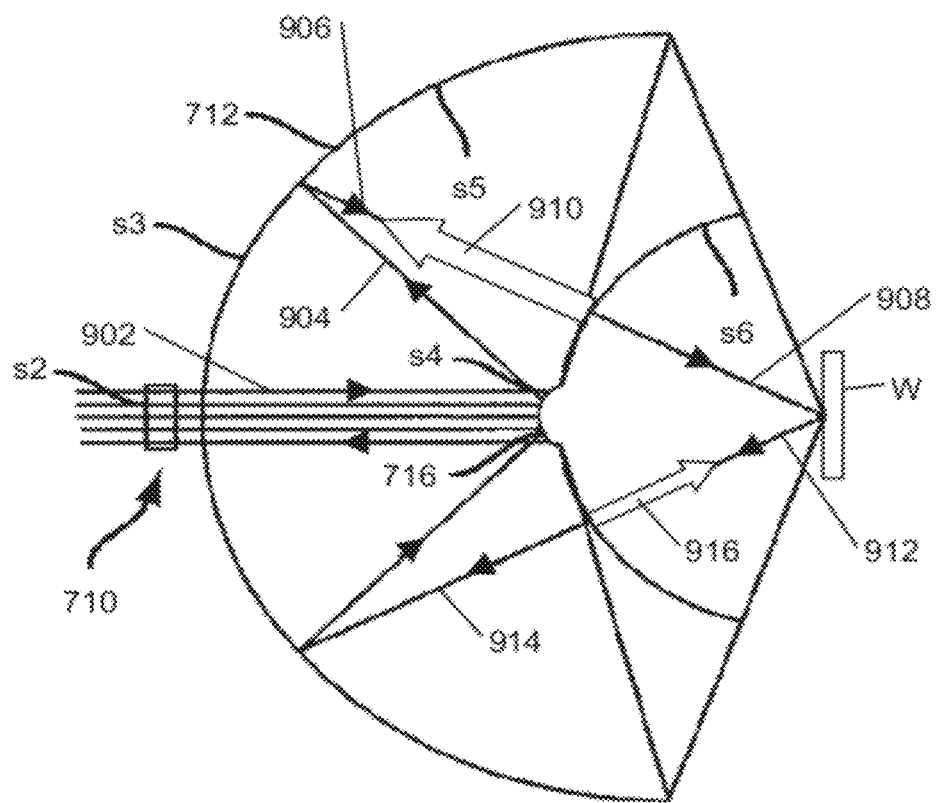
FIG. 9 depicts ghost reflections in a catadioptric optical objective with a monolithic element.

FIG. 9, according to an embodiment of the present invention, depicts ghost reflections in a catadioptric optical objective with a monolithic element. Features common to FIG. 7 are given the same labels. A ray of electromagnetic radiation 902 enters monolithic element 712 through the transparent portion of surface s3/s5. The ray is reflected from surface s4, as ray 904, then the reflective portion of surface s3, as ray 906. The ray 906 is directed by surface s3 towards curved surface s6 through which the ray passes 908 normal to the surface of s6. Reflection at the surface s6 gives rise to a first order ghost reflection 910 that is directed back along the path 906, 904 and 902.

As ray 908 is incident on the substrate W, reflected ray 912 then leaves the substrate W. Ray 912 is shown leaving substrate W at the same angle as incident ray 908, however, it will be appreciated that diffracted rays leave the substrate at a variety of angles. Ray 912 is directed towards curved surface s6 through which the ray passes 914 normal to the surface of s6. Reflection at the surface s6 gives rise to a second order ghost reflection 916 that is directed back along the path 912, 908, 906, 904 and 902.

The measured second order ghost reflection is of lower intensity compared to the first order ghost reflection, because it has been attenuated by additional transmission twice through surface s6 and reflection twice at substrate W, where radiation is absorbed and scattered.

Figure 10:
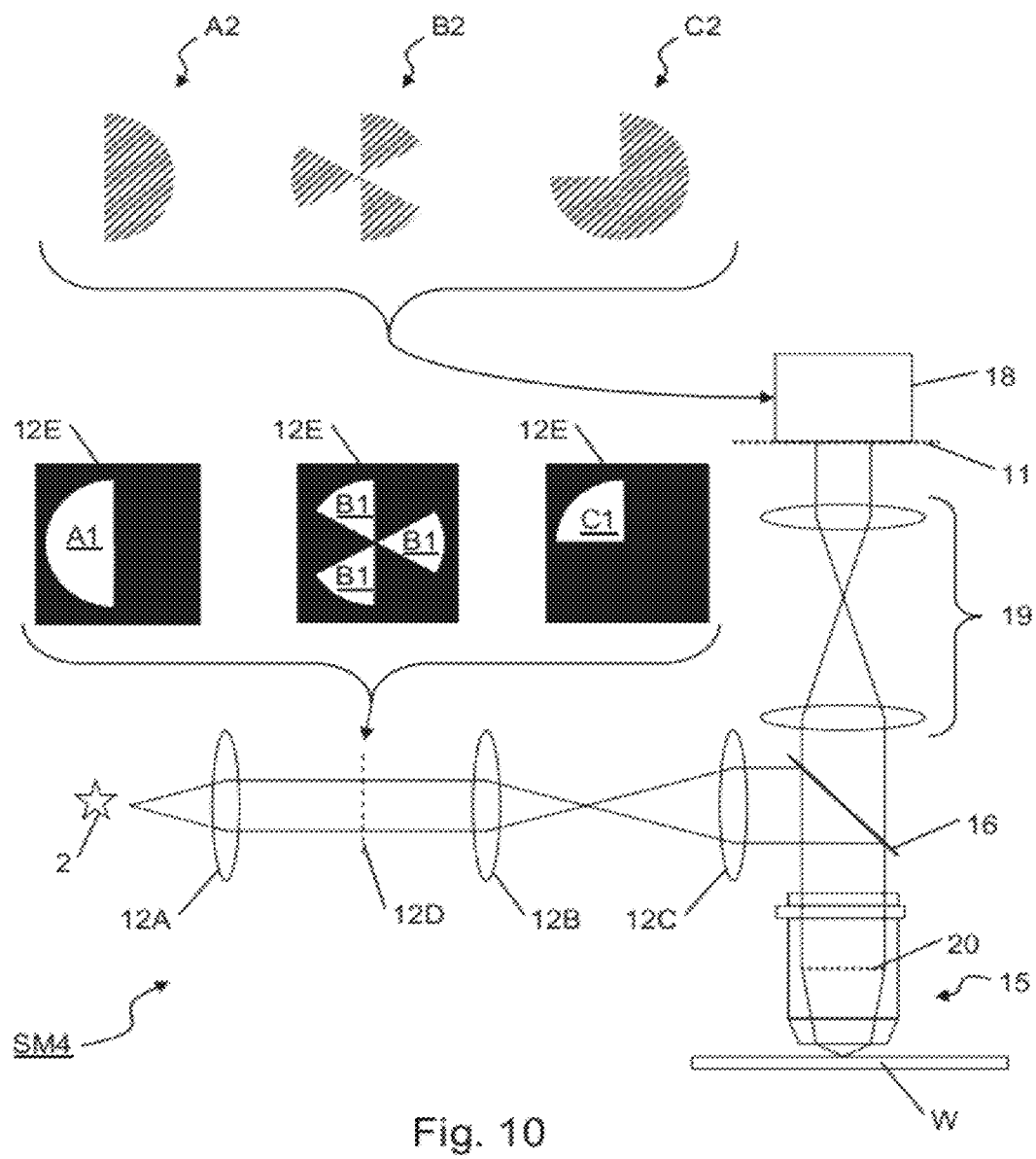
FIG. 10 depicts a scatterometer with pupil illumination and measurement, according to an embodiment of the present invention.

FIG. 10 depicts a scatterometer SM4 with pupil illumination and measurement, according to an embodiment of the present invention. Features common to FIGS. 4 and 5 are given the same labels.

The inspection apparatus SM4 has an illumination system 12A-12D configured to provide a beam of electromagnetic radiation by illuminating a first area A1 (or alternatively B1 or C1) in an illumination pupil plane 12D of the objective 15. The objective 15 is arranged with the illumination system 12A-12D to illuminate the substrate W with the beam of electromagnetic radiation. A detector 18 is configured to measure an angle resolved spectrum arising from the illumination of the substrate W, in a measurement area A2 (or B2 or C2 respectively) of a measurement pupil plane 11 of the objective excluding an area corresponding to the first area A1 (or B1 or C1 respectively).

Illumination apertures 12E are operable in the illumination pupil plane to define the first area A1, B1 or C1. In the case of illumination apertures 12E with A1 or B1 illuminated, the illumination system 12A-12D is configured to provide the beam of electromagnetic radiation without illuminating a second area of the illumination pupil plane, wherein the second area is an inversion of the first area through the centre of the illumination pupil plane 12D and the measurement area A2 or B2 corresponds to the second area.

In the case of an illumination aperture 12E with C1 illuminated, the illumination system 12A-12D is configured to provide the beam of electromagnetic radiation without illuminating a second area of the illumination pupil plane, wherein the second area is an inversion of the first area through the centre of the illumination pupil plane 12D, that is the opposite quadrant, and the measurement area C2 corresponds to the second area plus the remaining quadrants of the circle.

Thus, the ghost reflections are excluded from the angle-resolved spectrum measurement by using a partial pupil for the illumination and for the measurement excluding (for example by masking, filtering or disregarding) the area of the pupil plane that has been illuminated. The exclusion in the measurement step may be performed for example using an aperture in the measurement pupil plane or by the processor PU selecting a subset of the measurement data gathered across the whole detector.

The illumination aperture 12E may be configurable to optimally match a pattern to be measured by the illumination of the substrate. The illumination aperture 12E may be configurable for example by being automatically changeable, flexible or moveable in or out of the pupil plane. The pupil obscuration can be rotated to optimally match the orientation of the to be measured pattern on the substrate.

Compared to full illumination of the pupil plane, the partial illumination results in less light being available to measure the angle-resolved spectrum. In order to overcome this and to measure the full pupil, multiple illumination shots may be made with different illumination areas and corresponding measurement areas of the pupil plane. This may be done with two shots and rotating the aperture 12E illuminated with A1 (or B1 or C1) and rotating the measurement area A2 (or B2 or C2) both by 180 degrees between shots. In this case, to have high throughput, a fast aperture changer is useful.

Figure 11:
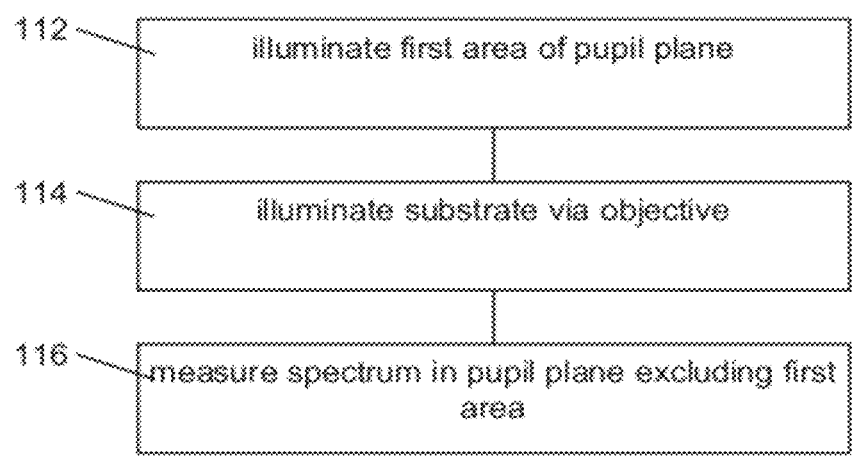
FIG. 11 is a flowchart of a method of inspection, according to an embodiment of the present invention.

FIG. 11 is a flowchart of a method of inspection of a substrate, according to an embodiment of the present invention. The first step 112 is providing a beam of electromagnetic radiation by illuminating a first area in an illumination pupil plane of an objective. The substrate is illuminated 114 with the beam of electromagnetic radiation via the objective. The angle resolved spectrum arising from the illumination of the substrate is measured 116 in a measurement area of a measurement pupil plane of the objective excluding an area corresponding to the first area.

It is possible to measure the ghost reflections only in the first area and use the results of such measurements to correct for measurements without partial illumination. Therefore in this embodiment there is provided an inspection apparatus for inspecting a substrate, the inspection apparatus including an illumination system configured to provide a beam of electromagnetic radiation by illuminating a first area in an illumination pupil plane of an objective, an objective arranged with the illumination system to illuminate the substrate with the beam of electromagnetic radiation, and a detector configured to measure an angle resolved spectrum arising from the illumination of the substrate, in a measurement area of a measurement pupil plane of the objective depending on the first area.

Figure 12:
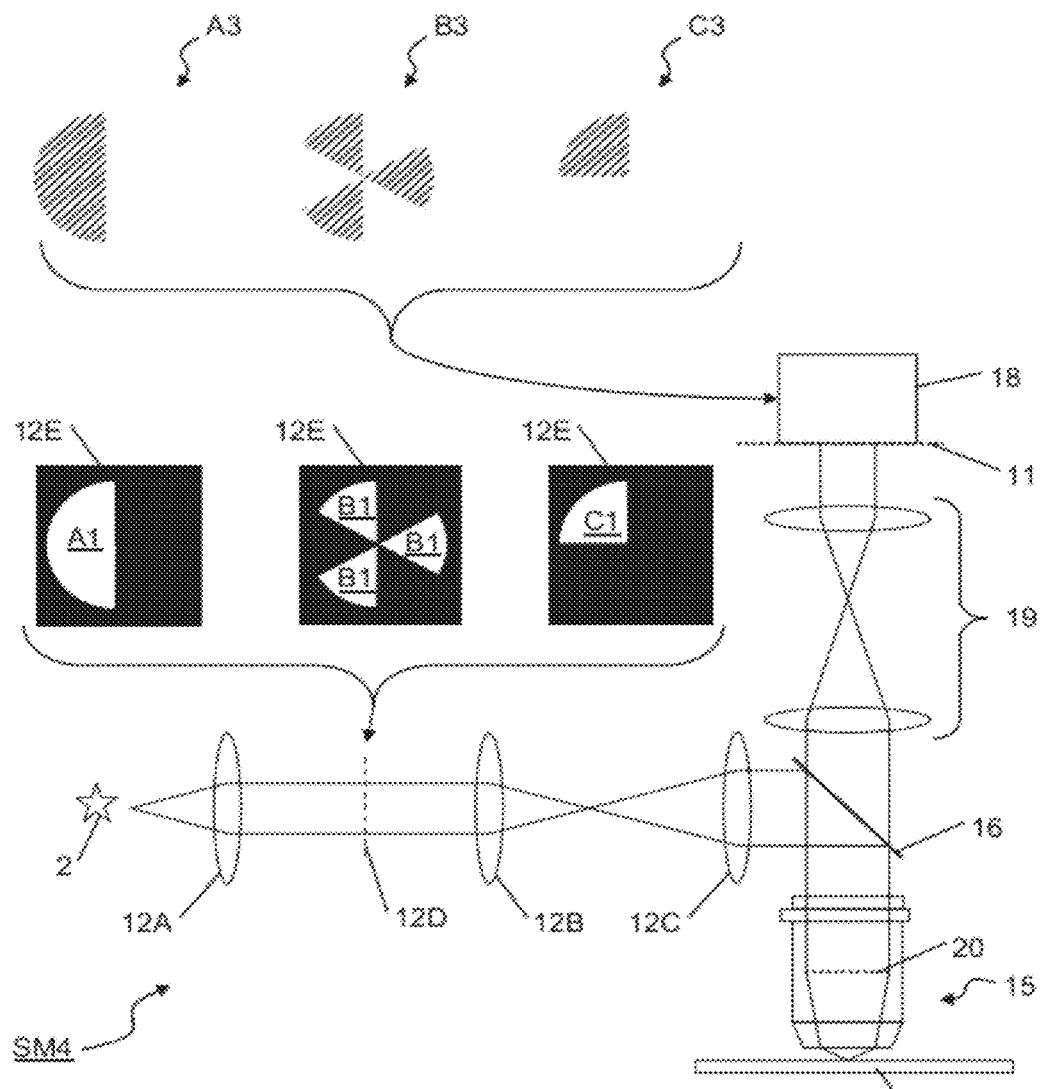
FIG. 12 depicts a scatterometer with pupil illumination and measurement, according to an embodiment of the present invention.

FIG. 12 depicts a scatterometer with pupil illumination and measurement, according to an embodiment of the present invention. The elements are labeled the same as for FIG. 10, except for measurement areas A3, B3 and C3 and wafer substrate W is replaced with a mirror M. The detector 18 is configured to measure an angle resolved spectrum arising from the illumination of the mirror M, in a measurement area A3 (or B3 or C3 respectively) of a measurement pupil plane 11 of the objective corresponding to the first partial area A1 (or B1 or C1 respectively) excluding the area of the pupil plane outside of the illumination area. No distinct points in the first area are an inversion of each other through the centre of the illumination pupil plane 12D. Therefore the reflected beam is not measured and only the ghost reflections are measured. These ghost reflections can be extrapolated across the whole measurement pupil plane by rotation around the centre of the measurement pupil plane, or by point inversion through the centre of the measurement pupil plane. Alternatively multiple measurements to cover the whole measurement pupil plane can be performed by rotating the aperture 12E, for example by rotating the aperture 12E illuminating with A1 (or B1 or C1) and rotating the measurement area A3 (or B3 or C3) both by 180 degrees between shots.

Figure 13:
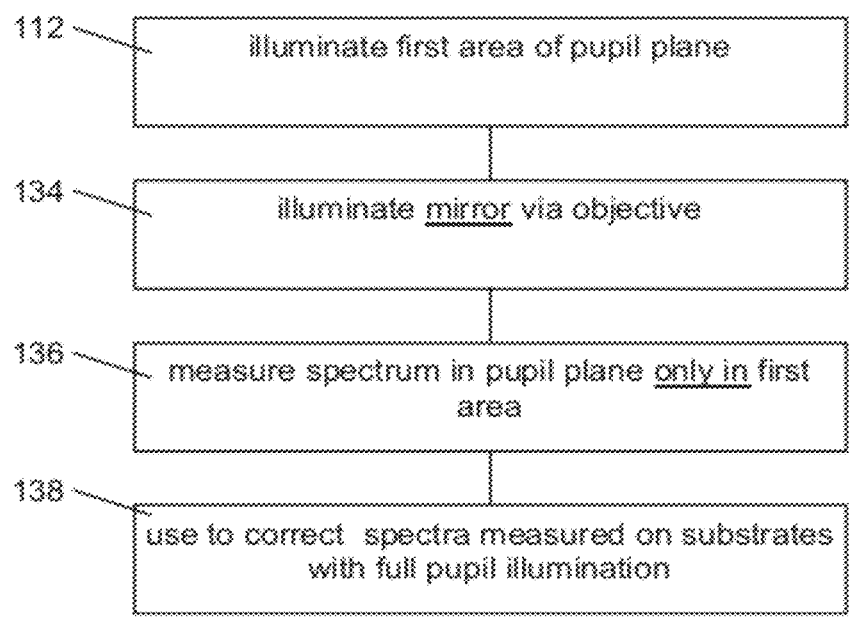
FIG. 13 is a flowchart of a method of inspection, according to an embodiment of the present invention.

FIG. 13 is a flowchart of a method of inspection, according to an embodiment of the present invention. Illumination step 112 is the same as for FIG. 11. However, in step 134, a mirror is illuminated and in step 136, the angle resolved spectrum arising from the illumination of the mirror is measured 116 in a measurement area of a measurement pupil plane of the objective corresponding to the first area in the illumination pupil plane. In step 138, the measurements obtained in step 136 can be used to correct for the ghost reflections, for example by subtracting those measurements from subsequent spectra obtained from product wafers with no illumination aperture 12E, before reconstruction is performed.

The embodiment described with reference to FIGS. 12 and 13 above is based on measurements on a mirror, M. The method is however not restricted to a measurement on a mirror but can also be applied to a reference measurement on a grating. For example, when a number of targets on a wafer that are substantially the same are to be measured, although the detailed structure of the targets will be different (for example, the CD or shape can vary over the wafer), the first order the pupil will not change. This means that the disturbance of the measuring signal through the reflections off the grating will be very small and can be neglected. Therefore it is possible to perform a calibration measurement as described with reference to FIGS. 12 and 13 (using a mirror substrate) but instead using a grating substrate. The measured ghost reflections can then be used to correct all measurements on the wafer substrate (or wafer lot) including the target used for calibration purposes.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens," where the context allows, may refer to any one or combination of various types of optical components, including refractive, reflective, magnetic, electromagnetic, and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g., semiconductor memory, magnetic or optical disk) having such a computer program stored therein.

For example, software functionalities of a computer system involve programming, including executable codes, may can be used to implement the above described inspection methods. The software code can be executable by a general-purpose computer. In operation, the code and possibly the associated data records can be stored within a general-purpose computer platform. At other times, however, the software may can be stored at other locations and/or transported for loading into an appropriate general-purpose computer system. Hence, the embodiments discussed above involve one or more software products in the form of one or more modules of code carried by at least one machine-readable medium. Execution of such codes by a processor of the computer system enables the platform to implement the functions in essentially the manner performed in the embodiments discussed and illustrated herein.

As used herein, terms such as computer or machine "readable medium" refer to any medium that participates in providing instructions to a processor for execution. Such a medium can take many forms, including but not limited to, non-volatile media, volatile media, and transmission media. Non-volatile media include, for example, optical or magnetic disks, such as any of the storage devices in any computer(s) operating as discussed above. Volatile media include dynamic memory, such as main memory of a computer system. Physical transmission media include coaxial cables, copper wire, and fiber optics, including the wires that comprise a bus within a computer system. Carrier-wave transmission media can take the form of electric or electromagnetic signals, or acoustic or light waves such as those generated during radio frequency (RF) and infrared (IR) data communications. Common forms of computer-readable media therefore include, for example: a floppy disk, a flexible disk, hard disk, magnetic tape, any other magnetic medium, a CD-ROM, DVD, any other optical medium, less commonly used media such as punch cards, paper tape, any other physical medium with patterns of holes, a RAM, a PROM, and EPROM, a FLASH-EPROM, any other memory chip or cartridge, a carrier wave transporting data or instructions, cables or links transporting such a carrier wave, or any other medium from which a computer can read or send programming codes and/or data. Many of these forms of computer readable media may be involved in carrying one or more sequences of one or more instructions to a processor for execution.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building storing blocks illustrating the implementation of specified functions and relationships thereof. The boundaries of these functional building storing blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An inspection apparatus for inspecting a substrate, comprising:
    an illumination system configured to provide a beam of electromagnetic radiation by illuminating a first area in an illumination pupil plane of an objective,
    the objective being configured to illuminate the substrate with the beam of electromagnetic radiation; and
    a detector configured to measure an angle resolved spectrum arising from the illumination of the substrate, in a measurement area of a measurement pupil plane of the objective excluding an area corresponding to the first area.

2. The inspection apparatus of claim 1, wherein:
    the illumination system is configured to provide the beam of electromagnetic radiation without illuminating a second area of the illumination pupil plane, wherein the second area is an inversion of the first area through the centre of the illumination pupil plane; and
    the measurement area corresponds to at least the second area.

3. The inspection apparatus of claim 1, further comprising a measurement aperture in the measurement pupil plane operable to exclude the area corresponding to the first area from the measurement pupil plane.

4. The inspection apparatus of claim 1, further comprising a processor configured to exclude the area corresponding to the first area from the measurement pupil plane by selecting a subset of measurement data from the detector.

5. The inspection apparatus of claim 1, wherein the objective comprises a curved surface through which the beam of electromagnetic radiation passes normal to the surface giving rise to first order ghost reflections.

6. The inspection apparatus of claim 1, wherein the objective comprises a curved surface through which electromagnetic radiation from the substrate passes normal to the surface giving rise to second order ghost reflections.

7. The inspection apparatus of claim 6, wherein the curved surface comprises a spherical surface.

8. The inspection apparatus of claim 1, wherein the illumination system comprises an illumination aperture operable in the illumination pupil plane to define the first area.

9. The inspection apparatus of claim 8, wherein the illumination aperture is configurable to optimally match a pattern to be measured by the illumination of the substrate.

10. A method of inspecting a substrate, the method comprising:
    providing a beam of electromagnetic radiation by illuminating a first area in an illumination pupil plane of an objective;
    illuminating the substrate with the beam of electromagnetic radiation via the objective; and
    measuring an angle resolved spectrum arising from the illumination of the substrate, in a measurement area of a measurement pupil plane of the objective excluding an area corresponding to the first area.

11. The method of claim 10, wherein:
    the providing the beam of electromagnetic radiation is performed without illuminating a second area of the illumination pupil plane, wherein the second area is an inversion of the first area through the centre of the illumination pupil plane; and
    the measurement area corresponds to at least the second area.

12. The method of claim 10, further comprising operating a measurement aperture in the measurement pupil plane to exclude the area corresponding to the first area from the measurement pupil plane.

13. The method of claim 10, further comprising excluding the area corresponding to the first area from the measurement pupil plane by selecting a subset of data measured in the measuring the angle resolved spectrum.

14. The method of claim 10, further comprising using an objective comprising a curved surface through which the beam of electromagnetic radiation passes normal to the surface giving rise to first order ghost reflections.

15. The method of claim 10, further comprising using an objective comprising a curved surface through which electromagnetic radiation from the substrate passes normal to the surface giving rise to second order ghost reflections.

16. The method of claim 15, wherein the curved surface comprises a spherical surface.

* * * * *